United States Patent
Gorra et al.

(10) Patent No.: US 9,758,750 B2
(45) Date of Patent: *Sep. 12, 2017

(54) ONE-HUNDRED PERCENT ALL NATURAL DISHWASHING COMPOSITION COMPRISING CITRUS FRUIT OR BERRY POWDER AND VINEGAR POWDER

(71) Applicants: George A. Gorra, Aventura, FL (US); Leila R. Gorra, Aventura, FL (US)

(72) Inventors: George A. Gorra, Aventura, FL (US); Leila R. Gorra, Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/275,559

(22) Filed: Sep. 26, 2016

(65) Prior Publication Data

US 2017/0009187 A1    Jan. 12, 2017

Related U.S. Application Data

(63) Continuation-in-part of application No. 14/187,044, filed on Feb. 21, 2014, now Pat. No. 9,458,418, which is a continuation-in-part of application No. 13/795,378, filed on Mar. 12, 2013, now Pat. No. 9,453,186.

(60) Provisional application No. 61/653,592, filed on May 31, 2012.

(51) Int. Cl.
| | |
|---|---|
| *C11D 7/44* | (2006.01) |
| *A01N 59/08* | (2006.01) |
| *A01N 37/02* | (2006.01) |
| *A01N 65/36* | (2009.01) |
| *C11D 3/04* | (2006.01) |
| *C11D 3/382* | (2006.01) |
| *A47L 15/00* | (2006.01) |
| *C11D 3/20* | (2006.01) |
| *C11D 7/26* | (2006.01) |

(52) U.S. Cl.
CPC ............... *C11D 7/44* (2013.01); *A01N 37/02* (2013.01); *A01N 59/08* (2013.01); *A01N 65/36* (2013.01); *A47L 15/0018* (2013.01); *C11D 3/046* (2013.01); *C11D 3/2079* (2013.01); *C11D 3/2086* (2013.01); *C11D 3/382* (2013.01); *C11D 7/265* (2013.01)

(58) Field of Classification Search
CPC .................................................... C11D 3/2075
See application file for complete search history.

(56) References Cited

U.S. PATENT DOCUMENTS

| | | | | |
|---|---|---|---|---|
| 6,734,155 | B1 * | 5/2004 | Herbots | C11D 3/2079 |
| | | | | 510/300 |
| 9,453,186 | B2 * | 9/2016 | Gorra | C11D 3/2082 |
| 9,458,418 | B2 * | 10/2016 | Gorra | C11D 7/44 |
| 2004/0253343 | A1 * | 12/2004 | Ha | A23L 27/14 |
| | | | | 426/17 |
| 2007/0031560 | A1 * | 2/2007 | Dubay | A23L 2/56 |
| | | | | 426/534 |
| 2012/0231031 | A1 * | 9/2012 | Pearson | A61K 31/10 |
| | | | | 424/195.17 |

* cited by examiner

*Primary Examiner* — Charles Boyer
(74) *Attorney, Agent, or Firm* — Robert M. Schwartz; Ted Whitlock

(57) ABSTRACT

A dishwashing composition which is a mixture of vinegar powder and lemon powder, or a mixture of vinegar powder, lemon powder and salt, for use in a dishwashing machine or for other cleaning purposes. The vinegar powder, lemon powder and, when present, salt can be mixed in any of a variety of proportions. The lemon powder, vinegar powder, and optional salt are non-toxic to humans and pets.

25 Claims, No Drawings

ONE-HUNDRED PERCENT ALL NATURAL DISHWASHING COMPOSITION COMPRISING CITRUS FRUIT OR BERRY POWDER AND VINEGAR POWDER

CROSS-REFERENCE TO RELATED APPLICATION

This application is a continuation-in-part of U.S. patent application Ser. No. 14/187,044, filed Feb. 21, 2014, entitled "All Natural Dishwashing Composition Comprising Lemon Powder and Vinegar Powder" which is a continuation-in-part of U.S. patent application Ser. No. 13/795,378, filed Mar. 12, 2013, entitled "All Natural Dishwashing Composition Comprising Lemon Powder, Vinegar Powder and Salt" and which claims priority from and the benefit of U.S. Provisional Patent Application Ser. No. 61/653,592 filed May 31, 2012, entitled "Dishwashing Composition," and which each of the aforementioned applications is incorporated herein in its entirety.

BACKGROUND OF THE INVENTION

The invention relates to a natural, non-toxic cleaning composition, substantially free from additives or preservatives. More particularly, the invention relates to a formulation of a cleaning composition which includes vinegar powder and lemon powder in any of a variety of proportions to be delivered in a measured pod, sachet, or tablet form for use in an automatic dishwasher. The composition can further include salt, preferably sea salt, and more preferably a primordial sea salt, such as Himalayan Sea Salt.

Many cleaning compositions are complex formulations of chemicals. Phosphates, oxygen based bleaching agents, chlorine-based bleaching agents, non-ionic surfactants, alkaline salts, anti-corrosion agents, sodium silicate, anti-foaming agents, ammonia, perfumes, anti-caking agents, starches, sand and other chemicals, such as additives or preservatives are commonly found in dishwashing detergents. Other prior art cleaning compositions are comprised of surfactants of various ionic charges (non-ionic, anionic and cationic), caustics, alcohols, and solvents.

Other prior art detergent formulations include harsh, synthetic and/or man-made chemicals. These and the above compounds could injure a person if ingested, or can be harmful to the environment when disposed with wastewater.

The current invention overcomes the disadvantages of the prior art by providing a cleaning composition, preferably useful in automatic dishwashing machines, which is safe to use, non-toxic to man or beast, and exceptionally cleans dishes or other objects which are desired to be cleaned.

SUMMARY OF THE INVENTION

The subject invention concerns a cleaning composition comprising lemon powder and vinegar powder. One embodiment of the composition of the invention is a cleaning composition useful as a dishwashing composition, and preferably useful as a dishwashing composition employed with the operation of an automatic dishwashing machine. One preferred embodiment of the invention can include a salt, preferably sea salt, and more preferably a primordial sea salt, such as Himalayan Sea Salt.

Preferably the lemon powder and vinegar powder ingredients are natural products, made or derived from a natural source, such as a plant source, e.g., lemon powder being derived from the fruit of a lemon tree and vinegar powder being derived from sugar cane. In an embodiment comprising salt, said salt is also preferably a natural product, such as sea salt, derived from a natural salt source. More preferably, the sea salt is derived from a deposit from a primordial sea. These natural-derived powders are advantageously useful in an automatic dishwasher for cleaning plates, silverware, food containers, or the like, used by humans and pets for eating and drinking, where it can be undesirable to use cleaners or detergents that contain harsh or harmful chemicals. The primordial sea salt can further be useful for its antibacterial properties and can serve to cleanse the automatic dishwasher during its operation.

In a preferred embodiment, the subject invention therefore provides a dishwashing composition comprising:
 a) lemon powder, and
 b) vinegar powder.

In another preferred embodiment, the subject invention provides a dishwashing composition comprising:
 a) lemon powder,
 b) vinegar powder, and
 c) salt, e.g., primordial sea salt.

The dishwashing composition can be admixed to provide a substantially homogenous mixture composition. Preferably, the composition comprises lemon powder and vinegar powder, or lemon powder, vinegar powder, and primordial sea salt, all of which are 100% derived from a natural source. More preferably, the composition is 100% free of additives or preservatives.

Vinegar powder is commercially available, and is commonly derived from sugar cane or other natural plant sources. Whereas bottled vinegar in liquid form typically has about 3%-5% acidity (i.e., about 3%-5% acetic acid in water), vinegar powder is preferably provided in fine powder form, and has at least 15%-25% acidity (15%-25% acetic acid) or higher, preferably having about 16%-18% acidity, wherein the high acidity can contribute to the cleansing action or potency of the composition comprising the vinegar powder. The vinegar powder is preferably not prepared by freeze-drying process, but can be provided in freeze-dried form.

The lemon powder is also commercially available, and is commonly derived from lemons. In a preferred embodiment, the lemon powder is provided in lyophilized, or freeze-dried, form and has from about 1.0% to about 10% acidity (i.e., about 1.0% to about 10% of the composition is citric acid), and preferably at least about 1.3% acidity. The lemon powder can further contribute to the acidity, and thus the cleaning action or potency of the overall composition.

Salt is also commercially available and is typically derived from solid deposits extracted from brine or sea water. A preferred salt is sea salt, more preferably primordial sea salt, which is found in deposits from ancient, primordial seawater, which is substantially free of contaminants or pollutants. For example, Primordial Ocean Salt Himalaya™ (POSH) is available from Posh Salt (Cliffside Park, N.J.)

The mixture of the composition can range from about 1-12 parts of vinegar powder to about 0.1-15 parts of lemon powder, and 0 to about 5 parts salt, by weight, wherein a preferred mixture for a dishwashing composition comprises about 9 parts vinegar powder to about 1 part lemon powder, by weight. The salt component can preferably be provided at about 0.25 parts in a mixture containing 9 parts vinegar powder and 1 part lemon powder.

The mixture can also be added to or dissolved in an aqueous solution, preferably water, to provide a cleansing spray composition for cleaning items or household areas.

The subject invention further concerns a method of using a dishwashing composition in a dishwashing machine, said method comprising the steps of:

a) placing soiled dishes in said dishwashing machine, b) placing a sufficient amount of the dishwashing composition of the invention inside the dishwashing machine, and c) operating the dishwashing machine in accordance with product instructions of the dishwashing composition and recommendations provided by a dishwashing machine manufacturer.

The acidity of the lemon powder and the vinegar powder may be higher or lower based on application and other considerations, such as the natural source of the components. These two primary powder ingredients are preferably mixed together at a ratio of about nine (9) parts vinegar powder to one (1) part lemon powder. Alternatively, the composition can further comprise about 0.25 parts salt. These admixed compositions, in powder form, can be dispensed within the dishwasher, for example, in the bottom of the dish reservoir, or placed in the detergent dispenser provided as part of the dishwashing machine.

Alternatively, the powder compositions can be compressed into a tablet shape, or contained in a packaging means for individual or single use, such as a pod, packet, pouch, or sachet. Preferably, such individual or single-use packaging comprises a water-soluble component which dissolves in water during the dishwashing process, allowing the powder to be dispensed and available for cleaning. The dishwashing machine can be operated in a conventional manner, pursuant to the operating instructions or recommendations for use provided by the manufacturer of the dishwashing machine.

The vinegar powder, lemon powder, and salt components of the compositions are comprised of a variety of chemical ingredients. Vinegar powder comprises, primarily, acetic acid ($HC_2H_3O_2$) which is a common component of liquid vinegar. Most over-the-counter vinegar products include about 5% acetic acid and 95% water.

Lemon powder primarily comprises citric acid ($H_3C_6H_5O_7$), which is found in lemons, limes, grapefruit, oranges, and other citrus fruits. Citric Acid constitutes about 8% of the dry weight of a lemon. Alternatively, the citrus or lemon powder can be substituted using a powder derived from another acidic fruit or berry source, so long as those sources provide appropriate acidity.

Sea salt, which is a preferred salt used in a composition of the invention generally comprises about 98% sodium chloride (NaCl), compared to table salt's 99.9% NaCl. Himalayan sea salt generally comprises about 95-96% sodium chloride, and about 2-3% polyhalite. The balance of the composition of sea salt and Himalayan sea salt (also known as halide salt) are trace minerals such as iron, magnesium, sulfur, or iodine. Himalayan sea salt can have a pink color due to the presence of iron oxide. When the lemon powder and the vinegar powder are mixed with water in the dishwasher, both acetic acid and citric acid (as well as other mild acids present in the fruit or berry source, e.g., malic acid, tartaric acid, or oxalic acid) will be formed in a mild state. Both of these mild acids are non-toxic, and both are commonly consumed daily, without harm to a person consuming the acids. In a composition comprising sea salt, alkalinity of the salt can affect (raise) the pH of the composition. Because the acidity of the vinegar powder and lemon powder contributes to the cleansing action of the composition, the salt component is preferably limited to the same amount as the amount of lemon powder and more preferably added at about 25% of the amount of lemon powder.

During operation of a dishwashing machine employing a composition of the invention, the action of the water and mild acids provides unexpectedly improved cleansing action for dishes, without adverse consequences to a sewage system or septic tank used in the disposal of waste-water.

Advantageously, a composition further comprising a salt component can provide antibacterial properties to the composition, and can further be advantageous as a cleansing agent for the dishwasher during its operation. With consideration given that acidic compositions can erode or tarnish certain metals, such as gold, a composition of the invention can also be used as a general cleanser for cleaning floors, walls, or household items without damage or harm to the item being cleaned or an item in the vicinity of the item being cleaned. For cleaning items having metal susceptible to highly acidic conditions, the composition can be diluted with water to decrease the strength of the composition.

In a preferred method of use for a dishwashing composition according to the subject invention in an automated dishwasher, the composition can provide more efficient cleansing effect, as has been observed, using cycle settings that provide water temperatures of 105° F. or greater, and/or wash cycles of at least 45 minutes, up to about two hours. For example, "Quick Wash" or "Economy" wash cycle settings may employ water temperatures of about 100° F. to about 104° F., and wash times of about 40 minutes. Automated dishwasher setting higher than "Quick Wash or Economy" are preferred for achieving greater cleansing efficacy using a composition of the invention.

DETAILED DESCRIPTION OF THE INVENTION

The invention concerns a composition comprising a mixture of a first component being vinegar powder, and a second component being a powder derived from a fruit or berry source, preferably a citrus fruit, e.g., lemon powder, to be employed as a cleansing powder. Preferably, the composition is employed as a dishwashing cleaner agent for use in a dishwashing machine.

Another embodiment of the invention comprises a mixture of a first component being vinegar powder, a second component being a powder derived from a fruit or berry source, preferably a citrus fruit, e.g., lemon powder, and a third component being salt, preferably sea salt and more preferably a primordial sea salt.

Each of these ingredients is preferably 100% derived from a natural source, preferably being substantially free, and more preferably being 100% free, of additives or preservatives.

This application refers to "vinegar powder" which is intended to mean powdered vinegar derived from any source, but preferably a natural source. It is understood that acetic acid is the primary active ingredient or component of "vinegar powder." Therefore, reference herein to "vinegar powder" is intended to encompass a powder form of vinegar, acetic acid, or a powder comprising acetic acid as its major or primary component.

This application also refers to "lemon powder" which is intended to mean a powder derived from a fruit or berry source. Citrus fruit, such as a lemon, lime, grapefruit, orange, tangerine, or the like, are useful because they are known to comprise relatively higher concentration of acid, e.g., citric acid, compared to other natural sources. The acidity of the fruit or berry source is not limited to citric acid, and can result from other natural acids contained in the natural fruit or berry source. For example, other fruits and berries, which may not be understood to be "citrus" fruits, can provide the necessary acidity to the composition and be substituted for, or combined with citrus or lemon powder.

Such other fruit and berry sources include, but are not limited to, cranberries (pH 2-3); apples, blueberries, cherries, grapes, nectarines, peaches, pears, pineapple, plums, or raspberries (pH 3-4); bananas (pH 4-5); and melons (pH about 6). These fruits and berries are known to contain one or more of citric acid, malic acid, tartaric acid, and oxalic acid, which provide acidity to the powder derived therefrom.

Advantageously, these citrus fruits and other fruit or berry sources for this powder component of the composition can provide fragrance consistent with the source fruit or berry. Adding more or less of one or more of the powders derived from a particular fruit or berry source, within the ranges provided herein, can provide an aesthetically pleasing scent or aroma to the final composition.

Accordingly, the terms "lemon powder," "citrus powder", or "citric acid powder," "fruit powder," "berry powder," or "fruit and berry powder" can be used interchangeably and refer to a powder form of the component derived from a natural source, such as citrus fruit, e.g., lemon, orange, lime, grapefruit, tangerine, or the like. Thus, reference herein to "lemon powder" or "citrus powder" would be understood to mean any natural powder derived from an "acidic" fruit or berry, having a measured pH below 7. The preferred fruit powders used for the subject composition are 100% natural, being free of additives or preservatives.

These terms are used to distinguish from other plant-derived (not fruit or berry-derived) acidic powders, such as the vinegar powder, which is derived from plants such as sugar cane, but are not derived from fruit or berry sources.

This application also refers to "salt" which is understood to refer to ionic compounds that can result from the neutralization reaction of an acid and a base. Salts are composed of related numbers of cations (positively charged ions) and anions (negative ions) so that the product is electrically neutral. The ionic components can be inorganic, such as sodium ($Na^+$) or chloride ($Cl^-$), as well as organic such as acetate ($C_2H_3O_2^-$), can be monatomic, e.g., fluoride ($F^-$), or polyatomic, e.g., sulfate ($SO_4^{2-}$). Salts are typically solids, and form crystals, at normal temperature and pressure.

Common salt-forming cations include:

Ammonium, $NH_4^+$; Calcium, $Ca^{2+}$; Iron, $Fe^{2+}$ or $Fe^{3+}$; Magnesium, $Mg^{2+}$; Potassium, $K^+$; Quaternary ammonium, $NR_4^+$; and Sodium, $Na^+$.

Common salt-forming anions include: Acetate, $CH_3COO^-$ (acetic acid); Bicarbonate, $HCO_3^-$; Carbonate, $CO_3^{2-}$ (carbonic acid); Chloride, $Cl^-$ (hydrochloric acid); Citrate, HOC (COO$^-$) ($CH_2COO^-)_2$ (citric acid); Cyanide, $C\equiv N^-$ (hydrocyanic acid); Fluoride, $F^-$ (hydrofluoric acid); Nitrate, $NO_3^-$ (nitric acid); Nitrite, $NO_2^-$ (nitrous acid); Phosphate, $PO_4^{3-}$ (phosphoric acid); or Sulfate, $SO_4^{2-}$ (sulfuric acid).

A preferred salt used in a composition of the subject invention is a natural salt or edible salt, which is primarily comprised of sodium chloride (NaCl). About 99.9% of table salt is NaCl.

Baking soda (sodium bicarbonate) is also a commonly used salt for cleansing, and is generally safe, being used in certain dentifrice compositions.

"Sea salt" is salt produced from the evaporation of seawater, and is commonly used in cooking and cosmetics. It is also called "bay salt" or "solar salt." Sea salt comprises about 85-98% NaCl, and about 2-15% trace minerals.

A preferred salt used in a composition of the invention is Himalayan sea salt derived from ancient, primordial seawater which provides a 100% all natural salt. Himalayan sea salt is a salt derived from ancient, primordial seawater. The chemical composition of Himalayan salt is about 95-96% sodium chloride, 2-3% polyhalite and small amounts of up to ten or more other minerals. A pink color often seen for Himalayan sea salt is due to the presence of a trace amount of iron oxide. A commercially available Himalayan sea salt is marketed as Primordial Ocean Salt Himalaya™ (POSH) by Posh Salt (Cliffside Park, N.J.). Himalayan sea salt is a marketing term for halite (commonly known as rock salt). Other Himalayan sea salts are also believed to be available from Pakistan.

An elemental analysis of the POSH product is reproduced below:

| Element | Concentration |
|---|---|
| Hydrogen | 0.30 g/kg |
| Lithium | 0.40 g/kg |
| Beryllium | <0.01 ppm |
| Boron | <0.001 ppm |
| Carbon | <0.001 ppm |
| Nitrogen | 0.024 ppm |
| Oxygen | 1.20 g/kg |
| Fluoride | <0.1 g/kg |
| Sodium | 382.61 g/kg |
| Magnesium | 0.16 g/kg |
| Aluminum | 0.661 ppm |
| Silicon | <0.1 g/kg |
| Phosphorus | <0.10 ppm |
| Sulfur | 12.4 g/kg |
| Chloride | 590.93 g/kg |
| Potassium | 3.5 g/kg |
| Calcium | 4.05 g/kg |
| Scandium | <0.0001 ppm |
| Titanium | <0.001 ppm |
| Vanadium | 0.06 ppm |
| Chromium | 0.05 ppm |
| Manganese | 0.27 ppm |
| Iron | 38.9 ppm |
| Cobalt | 0.60 ppm |
| Nickel | 0.13 ppm |
| Copper | 0.56 ppm |
| Zinc | 2.38 ppm |
| Gallium | <0.001 ppm |
| Germanium | <0.001 ppm |
| Arsenic | <0.01 ppm |
| Selenium | 0.05 ppm |
| Bromine | 2.1 ppm |
| Rubidium | 0.04 ppm |
| Strontium | 0.014 g/kg |
| Ytterbium | <0.001 ppm |
| Zirconium | <0.001 ppm |
| Niobium | <0.001 ppm |
| Molybdenum | 0.01 ppm |
| Technetium | unstable artificial isotope |
| Ruthenium | <0.001 ppm |
| Rhodium | <0.001 ppm |
| Palladium | <0.001 ppm |
| Silver | 0.031 ppm |
| Cadmium | <0.01 ppm |
| Indium | <0.001 ppm |
| Tin | <0.01 ppm |
| Antimony | <0.01 ppm |
| Tellurium | <0.001 ppm |
| Iodine | <0.1 g/kg |
| Cesium | <0.001 ppm |
| Barium | 1.96 ppm |
| Lanthan | <0.001 ppm |
| Cerium | <0.001 ppm |
| Praseodynium | <0.001 ppm |
| Neodymium | <0.001 ppm |

| Element | Concentration |
| --- | --- |
| Promethium | unstable artificial isotope |
| Samarium | <0.001 ppm |
| Europium | <3.0 ppm |
| Gadolinium | <0.001 ppm |
| Terbium | <0.001 ppm |
| Dysprosium | <4.0 ppm |
| Holmium | <0.001 ppm |
| Erbium | <0.001 ppm |
| Thulium | <0.001 ppm |
| Ytterbium | <0.001 ppm |
| Lutetium | <0.001 ppm |
| Hafnium | <0.001 ppm |
| Tantalum | 1.1 ppm |
| Wolfram | <0.001 ppm |
| Rhenium | <2.5 ppm |
| Osmium | <0.001 ppm |
| Iridium | <2.0 ppm |
| Platinum | 0.47 ppm |
| Gold | <1.0 ppm |
| Mercury | <0.03 ppm |
| Thallium | 0.06 ppm |
| Lead | 0.10 ppm |
| Bismuth | <0.10 ppm |
| Polonium | <0.001 ppm |
| Astat | <0.001 ppm |
| Francium | <1.0 ppm |
| Radium | <0.001 ppm |
| Actinium | <0.001 ppm |
| Thorium | <0.001 ppm |
| Protactinium | <0.001 ppm |
| Uranium | <0.001 ppm |
| Neptunium | <0.001 ppm |
| Plutonium | <0.001 ppm |

Another salt that can be used in the composition is Dead Sea Salt. Dead Sea salt refers to salt extracted or taken from the Dead Sea. Its mineral composition is also different, being only 12-18% sodium chloride. The Dead Sea's mineral composition can vary with season, rainfall, depth, and temperature. One analysis of a commercial Dead Sea Salt product measured a 2.5% sodium chloride content. Analysis results showed the Dead Sea's overall salt concentration as 340 g/L and the major ion concentrations were found to be as follows:

| Major ions of Dead Sea water | |
| --- | --- |
| Ion | Concentration (mg/L) |
| Chloride and Bromide | 230,400 |
| Magnesium | 45,900 |
| Sodium | 36,600 |
| Calcium | 17,600 |
| Potassium | 7,800 |

Commercially available Dead Sea salt can also be obtained from the mineral-rich mud of the Dead Sea. One analysis determined the following major minerals to be present in Dead Sea mud:

| Minerals of Dead Sea mud | |
| --- | --- |
| Mineral* | Content (percentage) |
| Silicon dioxide | 20 |
| Calcium oxide | 15.5 |
| Aluminum oxide | 4.8 |
| Magnesium oxide | 4.5 |
| Iron(III) oxide | 2.8 |
| Sodium oxide | 1.7 |
| Potassium oxide | 1.3 |
| Titanium(IV) oxide | 0.5 |
| Sulfur trioxide | 0.4 |
| Phosphorus pentoxide | 0.3 |
| Chloride | 6.7 |
| Bromide | 0.2 |

It is also understood that the vinegar powder or citrus powder or salt components of a composition of the invention can be synthetically derived using well-known chemical processes. These synthetic powders are also part of the invention, though natural source-derived powders are preferred.

In a preferred embodiment, the first component and second component are provided as a dry mixture in proportions ranging from about 1:1 to about 10:1 ratio of vinegar powder:citrus powder. Most preferred is a composition comprising a dry mixture of the first and second components at about nine (9) parts vinegar powder to one (1) part lemon powder. For example, a 1000 kg batch of a composition can be prepared by mixing 900 kg vinegar powder and 100 kg lemon powder. This composition is a preferred embodiment of a composition of the subject invention comprising two primary components: vinegar powder and citrus (e.g., lemon) powder, which works well in an automatic dishwashing machine.

In an embodiment comprising the above vinegar powder and lemon powder, and a third component, such as salt, the dry mixture is prepared in proportions of about 1:1:1 to about 10:1:0.1 of vinegar powder:citrus powder:salt. A preferred composition can be prepared by mixing 9 parts vinegar powder, 1 part lemon powder, and 0.25 parts Himalayan sea salt. Accordingly, a 1025 kg batch of a 3-component composition can be prepared by adding 900 kg vinegar powder, 100 kg lemon powder and 25 kg Himalayan sea salt. This composition is a preferred embodiment of a composition of the subject invention comprising three (3) primary components: vinegar powder, citrus (lemon) powder and (Himalayan) sea salt, which works well in an automatic dishwashing machine.

It is contemplated that the mixture of vinegar powder with lemon powder, or a mixture of vinegar powder, lemon powder, and sea salt, may have additional uses especially in the cleaning arts. When such mixtures are mixed with or dissolved in water and placed in a spray bottle, a non-toxic spray cleaner for glass, metal, counter tops, refrigerators, sinks, bathrooms and the like is provided. The mixture of vinegar powder and lemon powder comprises a scent which is mild and aesthetically pleasant to the sense of smell. The composition can also be used as an additive to other dishwashing products.

By altering the ratio of the first portion of the vinegar powder with the second portion of lemon powder, one may change the characteristics of the cleaning composition, allowing it to be used to clean other items. The composition may be employed in a clothes washing machine at one proportion of the mixture.

Being mildly acidic, the composition of the invention may also be useful as a safe, non-toxic material for opening clogged drains.

In certain concentrations at certain proportions, the mixture may be once again dissolved in water and could be sprayed on exposed limbs at an outdoor party, acting as an insect repellent. The mixture at other concentrations may be employed to keep insects out of the house or perhaps away from an outdoor party.

The mixture in other proportions may also be mixed with bath water to give the bather a soothing bath.

There are undoubtedly many other uses for the mixture of vinegar powder and lemon powder and salt. The examples here are in no way comprehensive, merely giving a general idea of the many possible uses this invention has. These examples are by no means limiting and are not intended to be comprehensive with respect to the mixture of vinegar powder and lemon powder and, alternatively, the salt.

Additionally, the ratios of the vinegar powder to lemon powder, or the ratios of vinegar powder/lemon powder/salt, described above are in no way limiting to the desired ratios of the invention. Although many uses may share the same ratio, other uses would employ other ratios. This invention contemplates the use of any possible ratio of vinegar powder to lemon powder being mixed together.

Several examples also described dissolving the mixture in water. This is in no way limiting either. It could be dissolved in any fluid which it is soluble in at any proportion and the uses such a composition are considered well within the scope of the invention.

Additionally, the mixture of vinegar powder with lemon powder may form the base for mixing in another or multiple powders. Further, these additional ingredients may form the basis for products which may include the group of cleaning products, but may also belong to other groups or sets of products. An example of such a mixture may be vinegar powder with lemon powder (at any appropriate proportion) mixed with a pharmaceutical. Such a mixture could be formed into a tablet, a liquid or other device to introduce a medicine or pharmaceutical into a human or animal.

Further, there are several physical properties of a white vinegar powder that has been considered for use in this invention. First, the white vinegar powder is preferably derived from sugarcane as known in the art, where it is from a fermented process made from sugar cane. Secondly, the white vinegar powder has an acidity of between 12-18.68%, which generally equates to 12-18.68 grams of acetic acid to 100 grams of white vinegar powder. It is to be understood that other sources and supplies of both white vinegar powder, lemon powder, acetic acid, citric acid, as well as any other ingredient either discussed or claimed exist and that this application contemplates the utility of their use if so desired. It is also contemplated in alternative embodiments that citric acid can be derived from other sources of naturally occurring citrus acid.

It is also contemplated that the natural ingredients will be from fresh lemons and fresh sugar cane. Preferably, the composition is 100% derived from natural sources.

Although the proportions of the composition components can be varied, as would be recognized and understood in the art, Himalayan sea salt or other salt used in the composition is generally mildly alkaline, so the proportional amount of the salt added to the composition is preferably limited to no more than equal parts with the acidic vinegar powder and citrus powder in order to maintain the cleaning properties of the composition. More preferably, any alkaline component of the composition is included at about 5% or less, preferably about 2.5% of the total composition.

In use, the preferred composition of vinegar powder and lemon powder, or the embodiment comprising vinegar powder, lemon powder, and sea salt, is placed in a pod or packet or pouch encased by a material comprising, at least in part, a water soluble component such as a water-soluble or water-disintegrable paper or polymeric covering, for containing the powder of the composition. Such packets are sometimes referred to and would be readily recognized in the art as "sachets."

Alternatively, the composition can be compressed to form a tablet which can be easily handled by a user. The tablet formation can include a binder or compression enhancer to facilitate the manufacturing process, or to facilitate holding the tablet together in unit doses for storage, shipping, or the like. A tablet comprising the subject composition as described herein can further include commonly used tablet ingredients, such as fillers, solubilizers, or the like, and can be coated with a clear, white, or color coating to provide integrity to the tablet or for an aesthetically pleasing look or feel to the tablet when handled by the user.

Preferably, the packet, pod or tablet containing the composition is provided as a single-use amount to be placed in the dishwasher prior to washing the dishes or other containers or items to be cleaned in the dishwasher. In use, the composition has cleaned dishes and glasses providing exceptional cleanliness, even when the dishes and containers were exceptionally soiled with hard-to-clean or dried-on foods.

The subject invention further includes a method of using a dishwashing composition in an automated dishwashing machine, the method comprising the steps of:

a) placing soiled dishes in said dishwashing machine,
b) placing a sufficient amount of said dishwashing composition comprising citrus powder and vinegar powder inside said dishwashing machine, and
c) operating said dishwashing machine in accordance with product instructions or recommendations provided by a dishwashing machine manufacturer.

The method can alternatively employ, in step b, above, a composition comprising citrus powder and vinegar powder, and a salt selected from the group consisting of table salt, baking soda, sea salt, primordial sea salt, Himalayan sea salt, and Dead Sea salt.

In a preferred method of use for a composition according to the subject invention in an automated dishwasher, the composition can provide more efficient cleansing effects, as observed, during cycle settings that provide water temperatures greater than 105° F., and/or wash cycles of at least 45 minutes, up to about two hours. For example, "Quick Wash" or "Economy" wash cycle settings may employ water temperatures of about 100° F. to about 104° F., and wash times of about 40 minutes.

Automated dishwasher setting higher than "Quick Wash or "Economy" are preferred for achieving greater cleansing efficacy using a composition of the invention.

Automated dishwasher settings are reflective of three general components: wash cycle time, water temperature, and water turbulence.

An example of typical operational settings for an automated dishwasher are shown below:

| Setting | Time (min.) | Temperature (° F.) | Turbulence |
|---|---|---|---|
| Pots/Pans | 120 | 161 | high |
| Intensive | 120 | 150 | high |
| Normal | 115-117 | 140 | medium |
| Delicate | 95-100 | 140 | medium/low |

-continued

| Setting | Time (min.) | Temperature (° F.) | Turbulence |
|---|---|---|---|
| Quick-Wash or Economy | 40-45 | 100-105 | medium |

Our observations of using the subject composition in an automated dishwashing machine show that settings which are not "Quick-Wash" or Economy provide preferred results or cleansing efficacy. Thus, a preferred use of a composition of the invention would employ a wash cycle which provides water temperature greater than 105° F. and cycle times greater than 45 minutes. For maximum efficiency, the composition would be used with any setting higher than a Quick/Wash or Economy setting.

Following the CLAIMS and ABSTRACT is an APPENDIX. The APPENDIX includes the material safety data sheets (MSDS) from the manufacturers of the vinegar powder and lemon powder ingredients and certificates of analysis (COA) from the manufacturers of those ingredients and the salt used in the preferred embodiments of this invention.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

We claim:

1. A dishwashing composition comprising:
   a) powder derived from citrus fruit or berry substantially free of additives or preservatives; and
   b) vinegar powder having acidity of about 12% to about 25%.

2. A dishwashing composition comprising:
   a) powder derived from citrus fruit or berry substantially free of additives or preservatives;
   b) vinegar powder having acidity of about 12% to about 25%; and
   c) salt.

3. The dishwashing composition of claim 2, wherein said salt is selected from the group consisting of table salt, baking soda, sea salt, primordial sea salt, Himalayan sea salt, and Dead Sea salt.

4. The dishwashing composition of claim 1 further comprising about 0.1 to about 10 parts salt.

5. A method of using a dishwashing composition in a dishwashing machine, said method comprising the steps of:
   a) placing soiled dishes in said dishwashing machine,
   b) placing a sufficient amount of said dishwashing composition of claim 1 inside said dishwashing machine, and
   c) operating said dishwashing machine in accordance with instructions or recommendations provided by a dishwashing machine manufacturer.

6. The method of claim 5 wherein the composition further comprises salt selected from the group consisting of table salt, baking soda, sea salt, primordial sea salt, Himalayan sea salt, and Dead Sea salt.

7. The method of claim 5 wherein the automated dishwashing machine is operated using a cycle which provides a water temperature greater than 105° F. and wash cycle time greater than 45 minutes.

8. A cleansing spray composition comprising a composition of claim 1 in aqueous solution.

9. The spray composition of claim 8, wherein the aqueous solution is water.

10. The spray composition of claim 5, wherein the ratio of vinegar powder to citrus fruit or berry powder is about 1:1 to about 10:1.

11. The composition of claim 8 wherein the ratio of vinegar powder to citrus fruit or berry powder is about 9:1.

12. The method of claim 5 wherein the citrus fruit powder is derived from a citrus fruit selected from the group consisting of lime, orange, grapefruit, or tangerine.

13. The composition of claim 8, further comprising salt selected from the group consisting of table salt, baking soda, sea salt, primordial sea salt, and Dead Sea salt.

14. The dishwashing composition of claim 1, wherein the citrus fruit or berry powder and vinegar powder are admixed to provide a substantially homogenous mixture composition.

15. The dishwashing composition as claimed in claim 1 wherein 100% of said citrus fruit or berry powder and said vinegar powder is derived from a natural source.

16. The dishwashing composition as claimed in claim 1 wherein said vinegar powder is derived from sugar cane.

17. The dishwashing composition as claimed in claim 1 wherein the citrus fruit powder is derived from a citrus fruit selected from the group consisting of lime, orange, grapefruit, or tangerine.

18. The dishwashing composition as claimed in claim 1 wherein said powder derived from citrus fruit or berry is freeze dried.

19. The dishwashing composition as claimed in claim 1, wherein said dishwashing composition comprises 1-12 parts of said vinegar powder to 0.1-15 parts of said citrus fruit or berry powder, by weight.

20. The dishwashing composition of claim 2, wherein the citrus fruit or berry powder and vinegar powder are admixed to provide a substantially homogenous mixture composition.

21. The dishwashing composition as claimed in claim 2 wherein 100% of said citrus fruit or berry powder and said vinegar powder is derived from a natural source.

22. The dishwashing composition as claimed in claim 2 wherein said vinegar powder is derived from sugar cane.

23. The dishwashing composition as claimed in claim 2 wherein the citrus fruit powder is derived from a citrus fruit selected from the group consisting of lime, orange, grapefruit, or tangerine.

24. The dishwashing composition as claimed in claim 2 wherein said powder derived from citrus fruit or berry is freeze dried.

25. The dishwashing composition as claimed in claim 2, wherein said dishwashing composition comprises 1-12 parts of said vinegar powder to 0.1-15 parts of said citrus fruit or berry powder, by weight.

* * * * *